(12) United States Patent
Breu et al.

(10) Patent No.: US 6,417,360 B1
(45) Date of Patent: Jul. 9, 2002

(54) HETEROCYCLIC SULFONAMIDES

(75) Inventors: Volker Breu, Schliengen (DE); Philippe Coassolo, Wittenheim; Werner Neidhart, Hagenthal le Bas, both of (FR); Sébastien Roux; Peter Weiss, both of Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/505,548

(22) Filed: Feb. 17, 2000

(30) Foreign Application Priority Data

Mar. 3, 1999 (EP) .............................. 99104306

(51) Int. Cl.[7] ............................................ C07D 401/14
(52) U.S. Cl. ....................................................... 544/319
(58) Field of Search ......................................... 544/319

(56) References Cited

U.S. PATENT DOCUMENTS 5,837,708 A 11/1998 Breu et al. .................. 514/274

FOREIGN PATENT DOCUMENTS

| EP | 0 713 875 | 5/1996 |
| EP | 0 897 914 | 2/1999 |
| WO | WO 96 19459 | 6/1996 |

*Primary Examiner*—John M. Ford
(74) *Attorney, Agent, or Firm*—George W. Johnson; John P. Parise

(57) ABSTRACT

The compounds of formula (I)

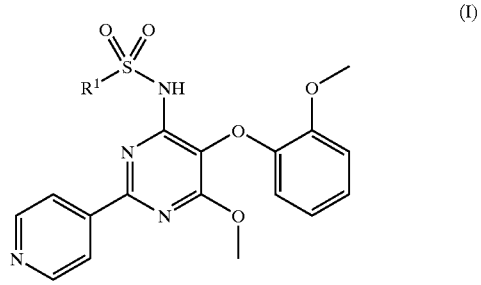

wherein $R^1$ has the significance as given in the description, are inhibitors of endothelin receptors and can therefore be used for the treatment of disorders which are associated with abnormal vascular tone and endothelial dysfunction.

1 Claim, No Drawings

HETEROCYCLIC SULFONAMIDES

BACKGROUND OF THE INVENTION

1. Field

The present invention relates to heterocyclic sulfonamides, methods for their manufacture, and their use as medicaments, especially for treating chronic heart failure.

2. Description

Sulfonamides are known inhibitors of endothelin receptors. See, for example, EP 0 713 875. There is a need for endothelin receptor inhibitors that have high antagonistic potency and achieve high plasma levels following oral administration.

SUMMARY OF THE INVENTION

The subject invention provides compounds of formula:

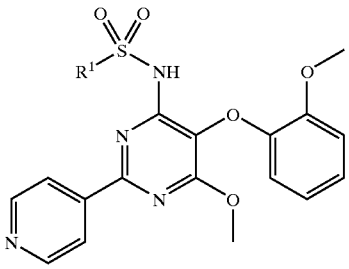

(I)

wherein $R^1$ is pyridyl, pyridyl substituted with lower alkyl, pyridyl substituted with lower alkenyl, thiazolyl, thiazolyl substituted with lower alkyl, or thiazolyl substituted with lower alkenyl;

and pharmaceutically usable salts of such compounds.

DETAILED DESCRIPTION OF THE PREFERRED EMBODIMENTS

The subject invention will now be described in terms of its preferred embodiments. These embodiments are set forth to aid in understanding the invention but are not to by construed as limiting.

The present invention relates to compounds of the formula (I)

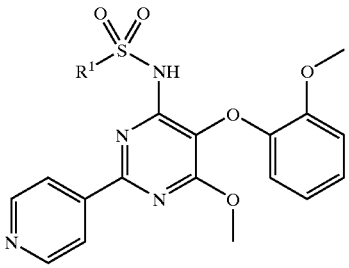

(I)

wherein $R^1$ is a heterocyclic residue selected from pyridyl and thiazolyl, where said heterocyclic residue may optionally be substituted with lower alkyl or lower alkenyl;
and pharmaceutically acceptable salts thereof.

The present invention also relates to a pharmaceutical composition comprising a compound of formula (I) and a pharmaceutically acceptable carrier and/or adjuvant.

Furthermore the present invention relates to the use of such compounds for the preparation of medicaments for the treatment or prophylaxis of disorders which are associated with abnormal vascular tone and endothelial dysfunction.

The present invention also relates to processes for the preparation of the compounds of formula (I).

In addition, the present invention relates to a method for the prophylactic and/or therapeutic treatment of disorders that are associated with abnormal vascular tone and endothelial dysfunction, which method comprises administering a compound of formula (I) to a human being or an animal.

The sulfonamides of the present invention are inhibitors of endothelin receptors. They can accordingly be used for the treatment of disorders which are associated with abnormal vascular tone and endothelial dysfunction. EP 0 713 875 discloses sulfonamide compounds as endothelin receptor inhibitors. However, the compounds of the present invention have a high antagonistic potency in vitro and show unexpectedly high plasma levels following oral administration.

Unless otherwise indicated the following definitions are set forth to illustrate and define the meaning and scope of the various terms used to describe the invention herein.

The term "lower alkyl" refers to a branched or straight chain monovalent saturated aliphatic hydrocarbon radical of one to seven carbon atoms, preferably one to four carbon atoms. This term is further exemplified by such radicals as methyl, ethyl, n-propyl, isopropyl, n-butyl, s-butyl, t-butyl and the like.

The term "lower alkenyl" refers to a lower alkyl group containing one or more double bond(s) in the alkylene chain.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non-toxic to living organisms. It also includes salts with inorganic or organic bases such as alkali salts like sodium and potassium salts, alkaline earth metal salts like calcium and magnesium salts, N-methyl-D-glutamine salts and salts with amino acids like arginine, lysine and the like.

More particularly, the present invention relates to compounds of the above formula (I), wherein $R^1$ is a heterocyclic residue selected from pyridyl and thiazolyl, where said heterocyclic residue may optionally be substituted with lower alkyl or lower alkenyl. The term "lower alkyl" preferably means methyl, ethyl, n-propyl, isopropyl, n-butyl, s-butyl or t-butyl, more preferably methyl, ethyl or isopropyl, still more preferably methyl or isopropyl, most preferably methyl. The term "lower alkenyl" preferably means vinyl, 1-propenyl, allyl, isopropenyl, 1-butenyl, 2-butenyl or 3-butenyl, more preferably vinyl, 1-propenyl, allyl and isopropenyl, most preferably isopropenyl.

Preferred heterocyclic residues in $R^1$ are 2-pyridyl and 2-thiazolyl, most preferred is 2-pyridyl. In a preferred embodiment, the heterocyclic residues in $R^1$ are substituted with lower alkyl or lower alkenyl, with lower alkyl being preferred.

Particularly preferred residues $R^1$ are 5-methyl-pyridine-2-yl, 5-isopropyl-pyridine-2-yl, 5-isopropenyl-pyridine-2-yl and 5-methyl-thiazol-2-yl. More preferred are 5-methyl-pyridine-2-yl, 5-isopropyl-pyridine-2-yl and 5-isopropenyl-pyridine-2-yl. Still more preferred are 5-methyl-pyridine-2-yl and 5-isopropyl-pyridine-2-yl. Most preferred is 5-methyl-pyridine-2-yl.

Particularly preferred compounds of formula (I) are 5-methyl-pyridine-2-sulfonic acid [6-methoxy-5-(2-methoxy-phenoxy)-2-pyridin-4-yl-pyrimidin-4-yl]-amide, 5-isopropyl-pyridine-2-sulfonic acid [6-methoxy-5-(2- methoxy-phenoxy)-2-pyridin-4-yl-pyrimidin-4-yl]-amide, 5-isopropenyl-pyridine-2-sulfonic acid [6-methoxy-5-(2-methoxy-phenoxy)-2-pyridin-4-yl-pyrimidin-4-yl]-amide and 5-methyl-thiazole-2-sulfonic acid [6-methoxy-5(2-methoxy-phenoxy)-2-pyridin-4-yl-pyrimidin-4-yl]-amide.

More particularly preferred compounds of formula (I) are 5-methyl-pyridine-2-sulfonic acid [6-methoxy-5-(2-methoxy-phenoxy)-2-pyridin-4-yl-pyrimidin-4-yl]-amide and 5-isopropyl-pyridine-2-sulfonic acid [6-methoxy-5-(2-methoxy-phenoxy)-2-pyridin-4-yl-pyrimidin-4-yl]-amide, most preferred is 5-methyl-pyridine-2-sulfonic acid [6-methoxy-5-(2-methoxy-phenoxy)-2-pyridin-4-yl-pyrimidin-4-yl]-amide.

The compounds of formula (I) can be prepared in analogy to known processes or processes described below and summarized in the following schemes 1 and 2:

4,6-Dichloro-5-(2-methoxy-phenoxy)-2-(pyridin-4-yl)-pyrimidine (described in EP 0/799 209) can be transformed to the intermediate of formula (III)—according to scheme 1—on reaction with an appropriate sulfonamide of formula (II), wherein $R^1$ is as defined in claim 1, in a suited solvent such as DMSO or DMF at room temperature or at elevated temperature and in the presence of a suited base such as potassium carbonate.

The corresponding sulfonamides can also be applied in above reaction in form of their pre-formed sodium or potassium salts.

Compounds of formula (III) can be further transformed to compounds of formula (I) by treatment with sodium methylate in a solvent such as methanol.

analogous to established procedures and/or can be derived from corresponding mercapto derivatives in analogy to a known reaction sequence comprising oxidation with $Cl_2$ in an acidic aqueous medium, such as diluted aqueous HCl, to yield the corresponding sulfonyl chlorides which can be transformed with liquid ammonia or aqueous ammonium hydroxide to the sulfonamides. The corresponding sodium or potassium salts can be obtained on treatment with sodium or potassium alkoxide in an appropriate solvent such as methanol.

Alternatively, compounds of formula (I) can be prepared—according to scheme 2—starting from 4-[4,6-dichloro-5-(2-methoxy-phenoxy)-pyrimidin-2-yl]-pyridine-1-oxide (preparation described in EP 0 799 209) in a reaction sequence analogous to that of scheme 1, to give compounds of formula (V).

Pyridine-N-oxide reduction of compounds of formula (V) can be accomplished with a reagent system such as $TiCl_4$/NaI in analogy to a method described in Chem. Ber. 123, 647 (1990), or with a trialkylsilyl chloride (for example, t-butyldimethylsilyl chloride) in the presence of a suited base, such as triethylamine, and with acetonitrile as a solvent. Other methods for pyridine-N-oxide deoxygenation are known per se and comprise, for example, catalytic hydrogenation or reduction with reducing agents such as trivalent phosphorus compounds or metals in acid. The Scheme 1

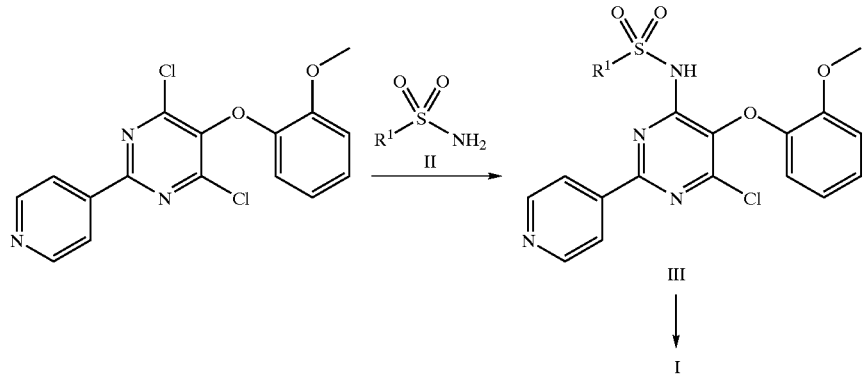

The heterocyclic sulfonamides of formula (II) are either already known in the literature, prepared in a manner conditions are a matter of choice and are readily determinable by the skilled artisan.

Scheme 2

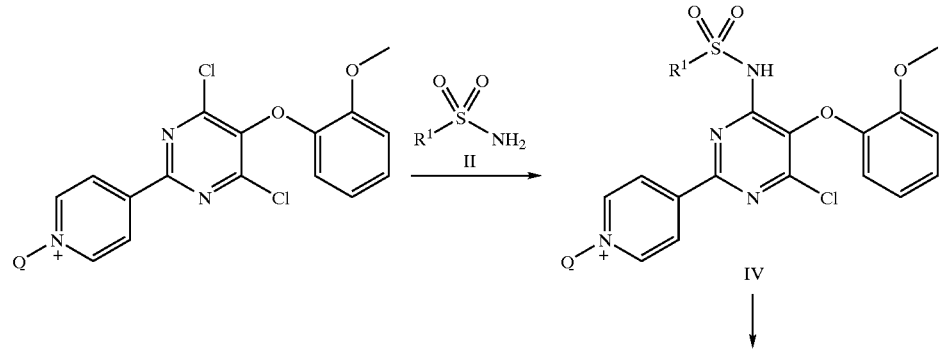

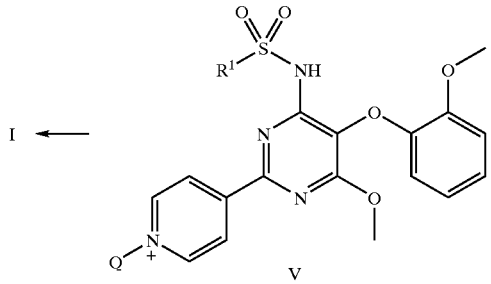

The intermediates of above formula (III) and formula (V), wherein R¹ is as defined above 1, preferably wherein R¹ is 5-methyl-pyridine-2-yl or 5-isopropyl-pyridine-2-yl, and the pharmaceutically acceptable salts thereof are new and are also subject of the present invention.

The inhibitory activity of the compounds of formula (I) on endothelin receptors can be demonstrated using the test procedures described hereinafter:

I. Inhibition of Endothelin Binding to Recombinant Human $ET_A$ Receptors Expressed in Baculovirus-infected Insect Cells A cDNA coding for human $ET_A$ receptors of human placenta was cloned (M. Adachi, Y.-Y. Yang, Y. Furuichi and C. Miyamoto, BBRC 180, 1265–1272) and expressed in the Baculovirus-insect cell system. Baculovirus-infected insect cells from a 23 l fermenter are centrifuged off (3000×g, 15 minutes, 4° C.) 60 hours after the infection, re-suspended in Tris buffer (5 mM, pH 7.4, 1 mM $MgCl_2$) and again centrifuged. After a further re-suspension and centrifugation the cells are suspended in 800 ml of the same buffer and freeze-dried at −120° C. The cells disintegrate when the suspension in this hypotonic buffer mixture is thawed. After a repeated freeze-drying/thawing cycle the suspension is homogenised and centrifuged (25000×g, 15 minutes, 4° C.). After suspension in Tris buffer (75 mM, pH 7.4, 25 mM $MgCl_2$, 250 mM sucrose) 1 ml aliquots (protein content about 3.5 mg/ml) are stored at −85° C.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM $MnCl_2$, 1 mM EDTA and 0.5% bovine serum albumin). 100 μl of this membrane suspension containing 70 μg of protein are incubated with 50 μl of $^{125}$I-endothelin (specific activity 2200 Ci/mMol) in assay buffer (25000 cpm, final concentration 20 pM) and 100 μl of assay buffer containing varying concentrations of test compound. The incubation is carried out at 20° C. for 2 hours or at 4° C. for 24 hours. The separation of free and membrane-bound radio-ligands is carried out by filtration over a glass fibre filter. The inhibitory activity of compounds of formula (I) determined in this test procedure is given in Table 1 as the $IC_{50}$, i.e. as the concentration [nM] which is required to inhibit 50% of the specific binding of $^{125}$I-endothelin.

TABLE 1

| Compound of example | 1 | 2 | 3 |
|---|---|---|---|
| $IC_{50}$ [nM] | ≤50 | ≤50 | ≤50 |

II. Inhibition of Endothelin-induced Contractions in Isolated Rat Aorta Rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% $O_2$ and 5% $CO_2$. The isometric stretching of the rings was measured. The rings were stretched to a pre-tension of 3 g. After incubation for 10 minutes with the test compound or vehicle cumulative dosages of endothelin-1 were added. The activity of the test compound was ascertained by the observed shift to the right of the dosage-activity curve of endothelin-1 in the presence of different concentrations of antagonist. This shift to the right (or "dose ratio", DR) corresponds to the quotient from the $EC_{50}$ values of endothelin-1 in the presence and in the absence of antagonist, with the $EC_{50}$ value denoting the endothelin concentration required for a half-maximum contraction.

The corresponding $pA_2$ value, which is a measure of the activity of the test compound, was calculated using a computer programme according to the following equation from the "dose ratio" DR for each individual dosage-activity curve.

$pA_2$=log(DR-1)-log(antagonist-concentration)

The $EC_{50}$ of endothelin in the absence of test compounds is 0.3 nM.

The $pA_2$ values obtained with compounds of formula (I) are given in the following Table 3.

TABLE 2

| Compound of example | 1 | 2 |
|---|---|---|
| $pA_2$ | ≧8.0 | ≧8.0 |

III. Pharmacokinetics of the Endothelin Receptor Antagonists

The pharmacokinetics of the newly synthesised endothelin receptor antagonists were assessed in Wistar rats. The test compounds were dissolved in DMSO at a concentration of 5 mg/mL and administered orally by gavage at a dose of 1 mL/kg body weight corresponding to 5 mg/kg body weight. Two rats were administered per test compound. Blood samples were collected from the retro-orbital sinus at 1 and 5 h post dose in one rat, and at 3 and 7 h post dose in the other rat. In addition a terminal 24 h blood sample was collected from both rats by heart puncture. Blood was collected on EDTA-NaF. Plasma was derived by centrifugation at 2000 g at +4° C. for 15 min. Plasma samples were assayed for active drug related material with a bioassay, based on the binding competition of tested compounds and $^{125}$I ET-1 on recombinant $ET_A$ receptors. Quantitation of plasma samples was by comparison to a calibration curve build up from control rat plasma spiked with known concentrations of the test compounds. Selected findings are summarised in the following table:

TABLE 3

| Test compound of example | Peak concentration in rat plasma (ng/mL) | Area under the plasma concentration time curve (ng · h/mL) |
| --- | --- | --- |
| 1 | ≧1'500 | ≧10'000 |

On the basis of their capability of inhibiting endogenous endothelin binding, the compounds of formula (I) can be used as medicaments for the treatment of disorders that are associated with abnormal vascular tone and endothelial dysfunction.

Therefore, the application field of the compounds of formula (I) could be heart failure (acute and chronic), systemic and pulmonary hypertension, acute ischaemic coronary syndrome, angina pectoris, renal failure (acute and chronic), organ transplant (e.g. liver, heart, kidney), cyclosporin nephrotoxicity, vasospastic disease (subarachnoid haemorrhage but also haemorrhagic and non-haemorrhagic stroke, Raynaud syndrome), peripheral artery occlusive disease, prevention of restenosis after stent or balloon angioplasty, septic shock or multiple organ failure as that occurring in intensive care, asthma, chronic obstructive pulmonary disease, gastric and duodenal ulcus, liver cirrhosis, pancreatitis (acute and chronic), inflammatory bowel disease, fibrosis, atheriosclerosis, obesity, glaucoma, prostatic adenoma, migraine, erectile dysfunction, adjunct to cancer therapy as well as other disorders associated with endothelin activities.

The compounds of formula (I) can also be administered in combination with antihypertensive drugs, antiarrhythmics, anti angina, antithrombotic and lipid lowering agents as well as antioxidants.

It will be appreciated that the compounds of formula (I) in this invention may be derivatised at functional groups to provide prodrug derivatives that are capable of conversion back to the parent compounds in vivo. Additionally, any physiologically acceptable equivalents of the compounds of general formula (I), which are capable of producing the parent compounds of general formula (I) in vivo, are within the scope of this invention.

As mentioned earlier, medicaments containing a compound of formula (I) are also an object of the present invention, as is a process for the manufacture of such medicaments, which process comprises bringing one or more compounds of formula (I) and, if desired, one or more other therapeutically valuable substances into a galenical administration form.

The pharmaceutical compositions may be administered orally, for example in the form of tablets, coated tablets, dragees, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as opthalmological preparations or as an aerosol, for example in the form of a spray.

For the preparation of tablets, coated tablets, dragees or hard gelatine capsules the compounds of the present invention may be admixed with pharmaceutically inert, inorganic or organic excipients. Examples of suitable excipients for tablets, dragees or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

It is a prerequisite that all adjuvants used in the manufacture of the preparations are non-toxic.

Preferred forms of use are intravenous, intramuscular or oral administration, most preferred is oral administration. The dosages in which the compounds of formula (I) are administered in effective amounts depend on the nature of the specific active ingredient, the age and the requirements of the patient and the mode of application. In general, dosages of about 0.01–10 mg/kg body weight per day come into consideration.

The following Examples shall illustrate preferred embodiments of the present invention but are not intended to limit the scope of the invention. Of the abbreviations used therein, MeOH signifies methanol, AcOEt signifies ethyl acetate, DMF signifies dimethylformamide, RT signifies room temperature, HPLC signifies high performance liquid chromatography, TLC signifies thin layer chromatography, ISN signifies Ion Spray Mass Spectrometry—negative mode, EI signifies Electron Impact Mass Spectrometry and M signifies molecular mass.

EXAMPLE 1 a) To a solution of 6.9 g sodium in MeOH (300 ml) were added 14.52 g of 5-methyl-pyridine-2-sulfonic acid [6-chloro-5-(2-methoxy-phenoxy)-2-pyridin-4-yl-pyrimidin-4-yl]-amide at RT and the mixture was refluxed for 5 days until completion of the reaction according to TLC analysis. The reaction mixture was concentrated in vacuo to half its volume upon which the crude reaction product precipitated as a sodium salt. It was filtered off by suction and dried in a high vacuum. The solid was dissolved in water, which was then made acidic by addition of acetic acid. The precipitating free sulfonamide was extracted into $Me_2Cl_2$. The organic layer was dried over $Mg_2SO_4$, concentrated on a rotary evaporator, and the crystalline solid that had formed was filtered off. It was then dried in a high vacuum for 12 h at 120° C. to give the desired 5-methyl-pyridine-2-sulfonic acid [6-methoxy-5-(2-methoxy-phenoxy)-2-pyridin-4-yl-pyrimidin-4-yl]-amide as white crystals. Melting point 225–226° C. ISN mass spectrum, m/e 478.2 (M-1 calculated for $C_{23}H_{21}N_5O_5S_1$: 478).

$C_{23}H_{21}N_5O_5S_1$: Calc: C 57.61; H 4.41; N 14.61; S 6.69. Found: C 57.56; H 4.38; N 14.61; S 6.83

Preparation of the starting material:

b) 11.3 g of 4,6-dichloro-5-(2-methoxy-phenoxy)-2-pyridin-4-yl)-pyrimidine and 19.66 g of 5-methylpyridyl-2-sulfonamide potassium salt (preparations described in EP 0 799 209) were dissolved in DMF (255 ml) under argon. The solution was stirred for 2 h at 40° C. until completion of the reaction according to TLC analysis. The reaction mixture was cooled to RT and the solvent removed in a high vacuum. The residue was suspended in water (850 ml), acetic acid (85 ml) was added and the mixture was stirred for 30 minutes at RT. The solid that precipitated was collected by filtration and dried in a high vacuum at 60° C. for 16 h to give 5-methyl-pyridine-2-sulfonic acid [6-chloro-5-(2-methoxy-phenoxy)-2-pyridin-4-yl-pyrimidin-4-yl]-amide as yellow crystals. Melting point 177–179° C. ISN mass spectrum, m/e 482.2 (M-1 calculated for $C_{22}H_{18}ClN_5O_5S_1$: 482).

EXAMPLE 2 a) In analogy to example 1a), from 5-isopropyl-pyridine-2-sulfonic acid [6-chloro-5-(2-methoxy-phenoxy)-2-pyridin-4-yl-pyrimidin-4-yl]-amide and NaOMe, there was obtained 5-isopropyl-pyridine-2-sulfonic acid [6-methoxy-5-(2-methoxy-phenoxy)-2-pyridin-4-yl-pyrimidin-4-yl]-amide as slightly yellow crystals. Melting point 195–197° C. ISN mass spectrum, m/e 506.2 (M-1 calculated for $C_{25}H_{25}N_5O_5S_1$: 506).

$C_{23}H_{21}N_5O_5S_1$: Calc: C 59.16; H 4.96; N 13.80; S 6.32. Found: C 58.99; H 4.90; N 13.83; S 6.37

Preparation of the starting material:

b) In analogy to example 1b), from 4,6-dichloro-5-(2-methoxy-phenoxy)-2-pyridin-4-yl)-pyrimidine and 5-isopropylpyridyl-2-sulfonamide potassium salt (preparation described in EP 799 209) there was obtained 5-isopropyl-pyridine-2-sulfonic acid [6-chloro-5-(2-methoxy-phenoxy)-2-pyridin-4-yl-pyrimidin-4-yl]-amide as a brown crystalline solid.

EXAMPLE 3 a) A solution of 0.156 g of 5-isopropenyl-pyridine-2-sulfonic acid [6-methoxy-5-(2-methoxy-phenoxy)-2-(1-oxy-pyridin-4-yl)-pyrimidin-4-yl]-amide in acetonitrile (2 ml) was treated at RT with 0.025 ml $TiCl_4$ followed by 0.135 g of sodium iodide and then stirred at RT for 20 h. Additional 0.1 ml of $TiCl_4$ were added, the mixture was refluxed for 1 h and then further 0.1 ml of $TiCl_4$ were added and refluxing was continued for 3 h to complete the reaction according to HPLC analysis. The reaction mixture was cooled to RT, concentrated on rotary evaporator, the residue taken up in AcOEt, which was washed with water, dried over $NaSO_4$ and finally removed in vacuo. The residue was purified by preparative thin layer chromatography, with AcOEt/MeOH: 9/1 as solvent system, to give the desired 5-isopropenyl-pyridine-2-sulfonic acid [6-methoxy-5-(2-methoxy-phenoxy)-2-pyridin-4-yl-pyrimidin-4-yl]-amide as a light yellow solid. ISN mass spectrum, m/e 504.2 (M-1 calculated for $C_{25}H_{23}N_5O_5S_1$: 504).

Preparation of the starting material:

b) To a solution of 5-isopropyl-pyridine-2-sulfonamide potassium salt (synthesis described in EP 799 209) in water (10 ml) were added 1.2 g of $KMnO_4$ at RT and the mixture was then refluxed for 30 minutes. The mixture was cooled to RT, acidified with diluted HCl and the product was extracted into AcOEt. The organic layer was washed with water, dried over $Na_2SO_4$ and concentrated in vacuo to give (5-(1-hydroxy-1-methyl-ethyl))-pyridine- 2-sulfonic acid amide as yellow oil. EI mass spectrum, m/e 216 (M calculated for: $C_8H_{12}N_2O_3S$ 216).

c) A solution of 0.1 g of (5-(1-hydroxy-1-methyl-ethyl))-pyridine-2-sulfonic acid amide in $CF_3CO_2H$ (2 ml) was refluxed for 20 h. The solvent was then removed in vacuo to give 5-isopropenyl-pyridine-2-sulfonic acid amide as a white solid which was essentially pure. EI mass spectrum, m/e 198 (M calculated for $C_8H_{10}N_2O_2S$: 198).

The corresponding potassium salt was prepared from the sulfonamide on treatment with potassium t-butylate in MeOH.

d) In analogy to example 1b), from 4-[4,6-dichloro-5-(2-methoxy-phenoxy)-pyrimidin-2-yl]-pyridine-1-oxide (synthesis described in EP 799 209) and 5-isopropenyl-pyridine-2-sulfonic acid amide potassium salt, there was obtained 5-isopropenyl-pyridine-2-sulfonic acid [6-chloro-5-(2-methoxy-phenoxy)-2-(1-oxy-pyridin-4-yl)-pyrimidin-4-yl]-amide as a light yellow solid. ISN mass spectrum, m/e 524.3 (M-1 calculated for $C_{24}H_{20}ClN_5O_5S$: 524).

e) In analogy to example 1a), from 5-isopropenyl-pyridine-2-sulfonic acid [6-chloro-5-(2-methoxy-phenoxy)-2-(1-oxy-pyridin-4-yl)-pyrimidin-4-yl]-amide and sodium methoxide there was obtained 5-isopropenyl-pyridine-2-sulfonic acid [6-methoxy-5-(2-methoxy-phenoxy)-2-(1-oxy-pyridin-4-yl)-pyrimidin-4-yl]-amide as a light yellow solid. ISN mass spectrum, m/e 520.2 (M-1 calculated for $C_{25}H_{23}N_5O_6S$: 520).

EXAMPLE 4 a) A suspension of 0.4 g of 5-methyl-thiazole-2-sulfonic acid [6-methoxy-5-(2-methoxy-phenoxy)-2-(1-oxy-pyridin-4-yl)-pyrimidin-4-yl]-amide in acetonitile (5 ml) was treated subsequently with 1.12 ml of triethylamine and 1.243 g of t-butyldimethylsilyl chloride at RT. The mixture was stirred 5 minutes at RT, its pH adjusted to neutral (by addition of trietylamine), and then heated to reflux for 60 h. The reaction mixture was cooled to RT and concentrated on a rotary evaporator. The residue was taken up in $CH_2Cl_2$, which was subsequently washed with acetic acid and water. The organic layer was dried over $MgSO_4$ and the solvent removed in vacuo. The residue was applied to a silica gel column with AcOEt/MeOH: 4/1 as eluent. Combination of the purified fractions and concentration in vacuo gave the desired 5-methyl-thiazole-2-sulfonic acid [6-methoxy-5-(2-methoxy-phenoxy)-2-pyridin-4-yl-pyrimidin-4-yl]-amide as a beige crystalline solid. ISN mass spectrum, m/e 484.2 (M-1 calculated for $C_{21}H_{19}N_5O_5S_1$: 484).

Preparation of the starting material:

b) 2.23 g of 5-methylene-thiazolidine-2-thione (preparation described in: Liebigs Ann. Chem., 1985, 58–64) were dissolved in 36% aqueous HCl (150 ml), cooled to −20° C. and $Cl_2$ was bubbled through the solution for 0.5 h while keeping its temperature below −20° C. Ether (400 ml cooled to −15° C.) was then added and after stirring for 5 minutes the layers were separated. The organic layer was treated with liquid $NH_3$ (200 ml) and the mixture allowed warming slowly to RT. The solvent was removed in vacuo to give 5-methyl-thiazole-2-sulfonic acid amide as an off-white solid. EI mass spectrum, m/e 178 (M calculated for $C_4H_6N_2O_2S_2$: 178).

The corresponding potassium salt was prepared from the sulfonamide on treatment with potassium t-butylate in MeOH.

c) In analogy to example 1b), from 5-methyl-thiazole-2-sulfonic acid amide potassium salt, and 4-[4,6-dichloro-5-(2-methoxy-phenoxy)-pyrimidin-2-yl]-pyridine-1-oxide there was obtained 5-methyl-thiazole-2-sulfonic acid [6-chloro-5-(2-methoxy-phenoxy)-2-(1-oxy-pyridin-4-yl)-pyrimidin-4-yl]-amide as a light yellow solid. ISN mass spectrum, m/e 504 (M-1 calculated for $C_{20}H_{16}ClN_5O_5S_2$: 504).

d) In analogy to example 1a), from 5-methyl-thiazole-2-sulfonic acid [6-chloro-5-(2-methoxy-phenoxy)-2-(1-oxy-pyridin-4-yl)-pyrimidin-4-yl]-amide and sodium methoxide there was obtained 5-methyl-thiazole-2-sulfonic acid [6-methoxy-5-(2-methoxy-phenoxy)-2-(1-oxy-pyridin-4-yl)-pyrimidin-4-yl]-amide as a light yellow solid. ISN mass spectrum, m/e 500.1 (M-1 calculated for $C_{21}H_{19}ClN_5O_6S_2$: 500).

Example A

Tablets containing the following ingredients can be produced in a conventional manner:

| Ingredients | mg per tablet |
| --- | --- |
| Compound of formula (I) | 10.0–100.0 |
| Lactose | 125.0 |
| Corn starch | 75.0 |
| Talc | 4.0 |
| Magnesium stearate | 1.0 |

Example B

Capsules containing the following ingredients can be produced in a conventional manner:

| Ingredients | mg per capsule |
| --- | --- |
| Compound of formula (I) | 25.0 |
| Lactose | 150.0 |
| Corn starch | 20.0 |
| Talc | 5.0 |

Example C

Injection solutions can have the following composition:

| | |
| --- | --- |
| Compound of formula (I) | 3.0 mg |
| Gelatine | 150.0 mg |
| Phenol | 4.7 mg |
| Water for injection | ad 1.0 ml |

Example D 500 mg of compound of formula (I) are suspended in 3.5 ml of Myglyol 812 and 0.08 g of benzyl alcohol. This suspension is filled into a container having a dosage valve. 5.0 g of Freon 12 are filled into the container under pressure through the valve. The Freon is dissolved in the Myglyol-benzyl alcohol mixture by shaking. This spray container contains about 100 single doses which can be applied individually.

Upon reading the present specification various alternative embodiments will become obvious to the skilled artisan. These variations are to be considered within the scope and spirit of the invention, which is only to be limited by the claims that follow and their reasonable equivalents.

What is claimed is:

1. The compound 5-methyl-pyridine-2-sulfonic acid [6-methoxy-5-(2-methoxy-phenoxy)-2-pyridin4-yl-pyrimidin-4-y]-amide or a pharmaceutically acceptable salt thereof.

* * * * *

UNITED STATES PATENT AND TRADEMARK OFFICE
CERTIFICATE OF CORRECTION

PATENT NO. : 6,417,360 B1
DATED : July 9, 2002
INVENTOR(S) : Breu et al.

It is certified that error appears in the above-identified patent and that said Letters Patent is hereby corrected as shown below:

Column 12,
Lines 38-41, please delete:
"1.     The compound 5-methyl-pyridine-2-sulfonic acid [6-methoxy-5-(2-methoxy-phenoxy)-2-pyridin4-yl-pyrimidin-4-y]-amide or a pharmaceutically acceptable salt thereof." and insert therefore:
-- 1.     The compound 5-methyl-pyridine-2-sulfonic acid [6-methoxy-5-(2-methoxy-phenoxy)-2-pyridin-4-yl-pyrimidin-4-yl]-amide or a pharmaceutically acceptable salt thereof. --

Signed and Sealed this

Nineteenth Day of November, 2002

*Attest:*

*Attesting Officer*

JAMES E. ROGAN
*Director of the United States Patent and Trademark Office*